(12) United States Patent
Prospere

(10) Patent No.: US 12,029,809 B2
(45) Date of Patent: Jul. 9, 2024

(54) HAIR OR SKIN TREATMENT COMPOSITION AND METHODS OF PREPARATION AND USE

(71) Applicant: Pauleine Prospere, Deerfield Beach, FL (US)

(72) Inventor: Pauleine Prospere, Deerfield Beach, FL (US)

(*) Notice: Subject to any disclaimer, the term of this patent is extended or adjusted under 35 U.S.C. 154(b) by 171 days.

(21) Appl. No.: 17/344,077

(22) Filed: Jun. 10, 2021

(65) Prior Publication Data
US 2022/0395450 A1 Dec. 15, 2022

(51) Int. Cl.
*A61K 8/92* (2006.01)
*A61K 8/23* (2006.01)
*A61K 8/31* (2006.01)
*A61Q 5/12* (2006.01)

(52) U.S. Cl.
CPC ............... *A61K 8/922* (2013.01); *A61K 8/23* (2013.01); *A61K 8/31* (2013.01); *A61K 8/925* (2013.01); *A61Q 5/12* (2013.01); *A61K 2800/805* (2013.01)

(58) Field of Classification Search
None
See application file for complete search history.

(56) References Cited

U.S. PATENT DOCUMENTS

| 6,048,520 A | 4/2000 | Hoshowski | |
| 6,479,060 B1 * | 11/2002 | Jones | A61K 8/922 |
| | | | 424/59 |
| 8,282,910 B2 | 10/2012 | Oguchi | |
| 2013/0072172 A1 | 3/2013 | Chang | |
| 2017/0189323 A1 * | 7/2017 | Ballenas | A61Q 17/04 |

FOREIGN PATENT DOCUMENTS

| CA | 2890395 A1 * | 5/2013 | ............. A01N 31/02 |
| WO | WO2001005363 | 1/2001 | |
| WO | WO2013149323 | 10/2013 | |

* cited by examiner

*Primary Examiner* — David J Blanchard
*Assistant Examiner* — Sarah J Chickos

(57) ABSTRACT

A hair or skin treatment composition for improving health of hair or skin includes an ointment obtained by heating one or more of castor oil, animal fat, and vegetable oil with a mash comprising one or more of carrots, onions, coconut flesh, and watercress, for between one and eight hours to generate, after straining to remove solids, a preliminary oil mixture. The preliminary oil mixture is heated with one or more of citrus juice and nutmeg, for between one and eight hours, to generate, after straining to remove solids, an intermediate oil mixture. The intermediate oil mixture is heated with sulfur, petrolatum, and at least one agent configured for absorbing or blocking ultraviolet radiation to generate, upon cooling, the ointment, which can be applied to hair or skin of a user to effect a physical or aesthetic change thereto.

10 Claims, 2 Drawing Sheets

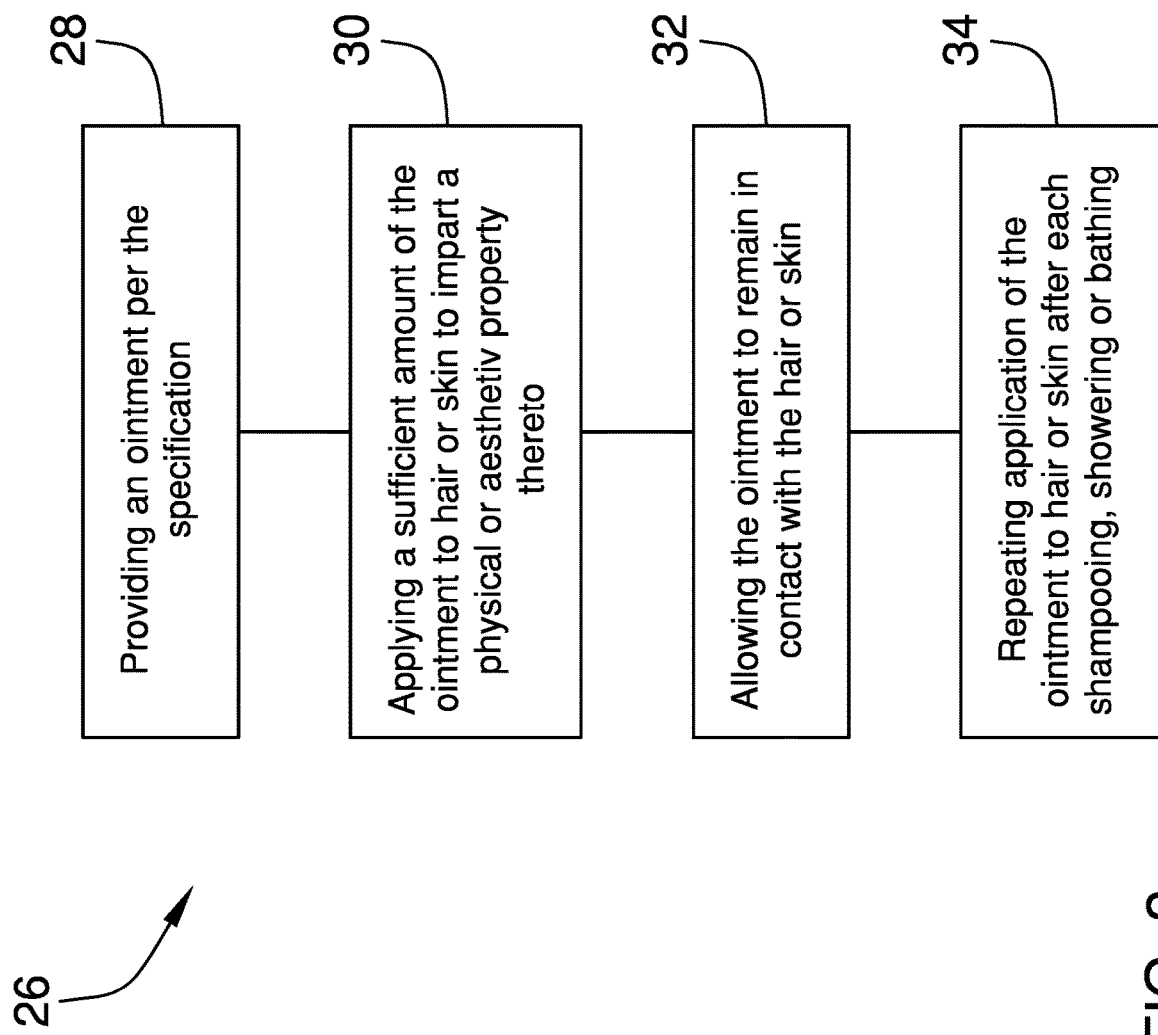

HAIR OR SKIN TREATMENT COMPOSITION AND METHODS OF PREPARATION AND USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to treatment compositions and more particularly pertains to a new treatment composition for improving health of hair or skin. The present invention discloses a treatment composition for hair or skin comprising petrolatum, sulfur, an ultraviolet light absorbing or reflecting agent, and oils derived from animals, castor and cocoa beans, carrots, onions, coconut flesh, watercress, lemon, and nutmeg.

(2) Description of Related Art Including Information Disclosed Under 37 CFR 1.97 and 1.98

The prior art relates to treatment compositions. Prior art treatment compositions for hair or skin may comprise encapsulated conditioners, sunscreens, and aqueous solutions of hydrophilic compounds. What is lacking in the prior art is a treatment composition for hair or skin comprising petrolatum, sulfur, an ultraviolet light absorbing or reflecting agent, and oils derived from animals, castor and cocoa beans, carrots, onions, coconut flesh, watercress, lemon, and nutmeg.

BRIEF SUMMARY OF THE INVENTION

An embodiment of the disclosure meets the needs presented above by generally comprising an ointment obtained by heating one or more of castor oil, animal fat, and vegetable oil with a mash comprising one or more of carrots, onions, coconut flesh, and watercress, for between one and eight hours to generate, after straining to remove solids, a preliminary oil mixture. The preliminary oil mixture is heated with one or more of citrus juice and nutmeg, for between one and eight hours, to generate, after straining to remove solids, an intermediate oil mixture. The intermediate oil mixture is heated with sulfur, petrolatum, and at least one agent configured for absorbing or blocking ultraviolet radiation to generate, upon cooling, the ointment, which is configured for application to hair or skin of a user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 2 is a flow diagram for a method of treating hair or skin using an embodiment of the disclosure.

DETAILED DESCRIPTION OF THE INVENTION

Figure 1:
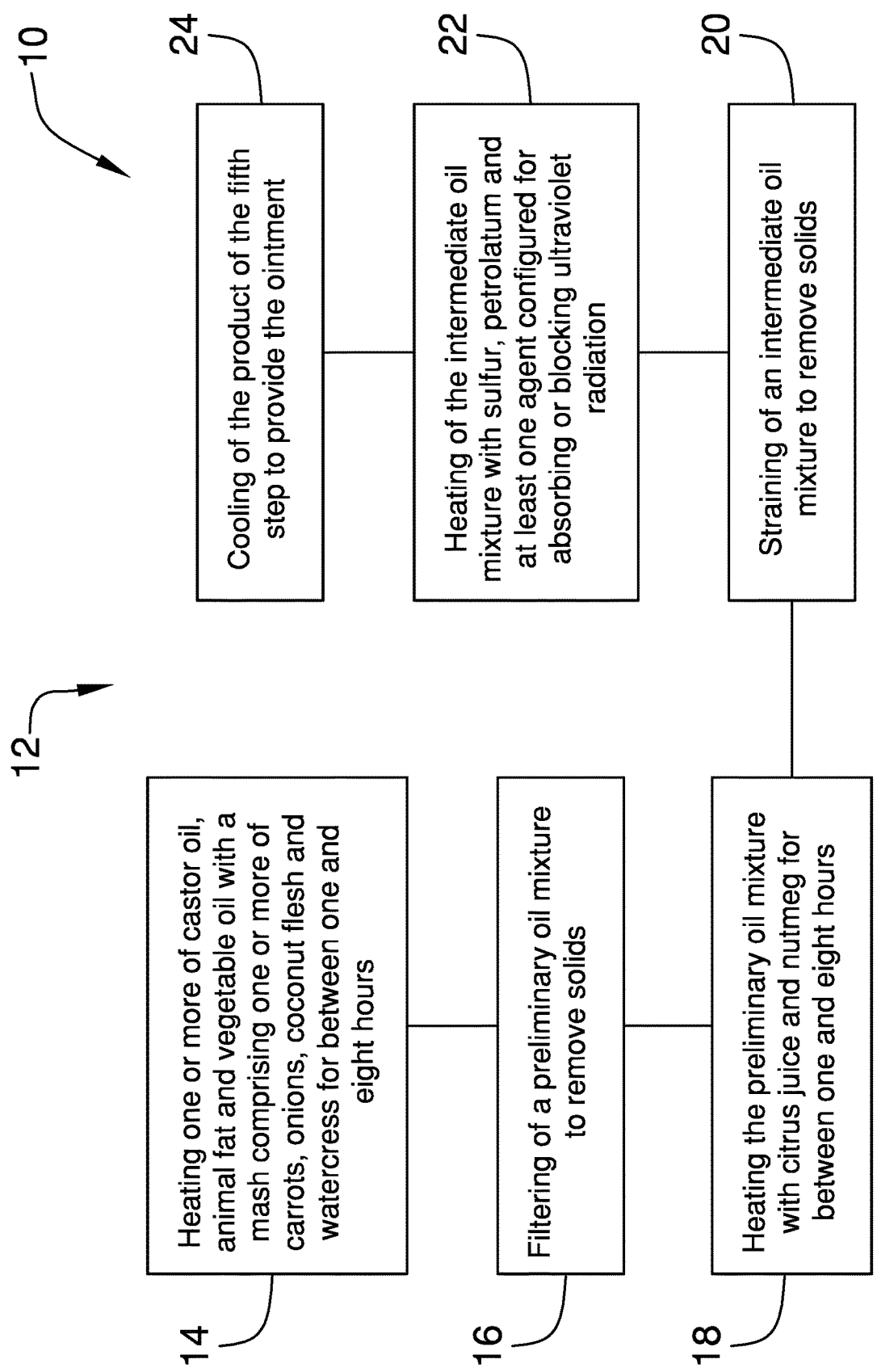
FIG. 1 is a flow diagram for a method of preparing a hair or skin treatment composition according to an embodiment of the disclosure.

With reference now to the drawings, and in particular to FIGS. 1 through 2 thereof, a new treatment composition embodying the principles and concepts of an embodiment of the disclosure and generally designated by the reference numeral 10 will be described.

As best illustrated in FIGS. 1 through 2, the hair or skin treatment composition 10 generally comprises an ointment obtained by heating one or more of castor oil, animal fat, and vegetable oil with a mash comprising one or more of carrots, onions, coconut flesh, and watercress, for between one and eight hours to generate, after straining to remove solids, a preliminary oil mixture. The preliminary oil mixture is heated with one or more of citrus juice and nutmeg, for between one and eight hours, to generate, after straining to remove solids, an intermediate oil mixture. The intermediate oil mixture is heated with sulfur, petrolatum, and at least one agent configured for absorbing or blocking ultraviolet radiation to generate, upon cooling, the ointment, which is configured for application to hair or skin of a user.

In one embodiment, the preliminary oil mixture is derived from Haitian castor oil, chicken oil, cocoa oil, carrots, onions, coconut flesh, and watercress. In another embodiment, the intermediate oil mixture is derived from the preliminary oil mixture, lemon juice, and one of ground nutmeg and powdered nutmeg. In yet another embodiment, the at least one agent configured for absorbing or blocking ultraviolet radiation comprises avobenzone, homosalate, octisalate, and octocrylene.

The preliminary oil mixture may comprise from 16.00 to 21.00 weight percent Haitian castor oil, for example 18.60 weight percent Haitian castor oil. The preliminary oil mixture may comprise from 16.00 to 21.00 weight percent grams chicken oil, for example 18.60 weight percent chicken oil. The preliminary oil mixture may comprise from 4.00 to 6.50 weight percent cocoa oil, for example 5.30 weight percent cocoa oil.

The mash component of the preliminary oil mixture may comprise from 7.50 to 10.00 weight percent carrots, for example 8.80 weight percent shredded carrots. The mash component of the preliminary oil mixture may comprise from 15.00 to 20.00 weight percent onions, for example 17.70 weight percent shredded onions. The mash component of the preliminary oil mixture may comprise from 0.00 to 16.00 weight percent coconut flesh, for example 13.30 weight percent grated coconut flesh. The mash component of the preliminary oil mixture may comprise from 15.00 to 20.00 weight percent watercress, for example 17.70 weight percent watercress.

The preliminary oil mixture may be obtained by heating the one or more of castor oil, animal fat, and vegetable oil and the mash comprising the one or more of carrots, onions, coconut flesh, and watercress at 80.0 to 100.0° C. for four hours.

The castor oil and cocoa oil may be obtained from commercial sources, or freshly prepared from Haitian castor and cocoa beans, respectively, using methods well known to those skilled in the art of extracting oils from beans. Similarly, the chicken oil may be obtained from commercial sources, or freshly prepared from chicken fat.

The mash components may be obtained from commercial sources, or freshly prepared by methods well known to those skilled in art of preparing vegetable mashes. The oils from the mash are extracted into the castor, cocoa, and chicken oil during heating.

The intermediate oil mixture may comprise from 85.00 to 96.00 weight percent of the preliminary oil mixture, based on total weight of components thereof prior to heating. For example, intermediate oil mixture may comprise 93.60 weight percent of the preliminary oil mixture, based on total weight of components thereof prior to heating.

The intermediate oil mixture also may comprise 3.00 to 8.00 weight percent lemon juice, for example, 5.20 weight percent lemon juice. The intermediate oil mixture also may comprise 0.50 to 2.00 weight percent of ground or powdered nutmeg, for example 1.20 weight percent of ground or powdered nutmeg.

The intermediate oil mixture may be obtained by heating the preliminary oil mixture and the one or more of citrus juice and nutmeg at 100.0 to 150.0° C. for four hours. The lemon juice and ground or powdered nutmeg may be obtained from commercial sources, or freshly prepared by squeezing lemons or crushing nutmegs. The oils therefrom are extracted into the preliminary oil mixture during heating.

The ointment may comprise from 80.00 to 90.00 weight percent of the intermediate oil mixture, based on total weight of components thereof and the components of the preliminary oil mixture prior to heating. For example, the ointment may comprise 84.70 weight percent of the intermediate oil mixture, based on total weight of components thereof and the components of the preliminary oil mixture prior to heating.

The ointment also may comprise 0.10 to 0.50 weight percent sulfur, for example 0.30 weight percent sulfur. The ointment also may comprise 10.0 to 20.0 weight percent petrolatum, for example 14.50 weight percent petrolatum. The ointment also may comprise 0.03 to 0.09 weight percent avobenzone, for example 0.06 weight percent avobenzone.

The ointment also may comprise 0.10 to 0.20 weight percent homosalate, for example 0.14 weight percent homosalate. The ointment also may comprise 0.10 to 0.20 weight percent octisalate, for example 0.12 weight percent octisalate. The ointment also may comprise 0.10 to 0.20 weight percent octocrylene, for example 0.16 weight percent octocrylene.

The ointment also may comprise one or more of lanolin, sorbitan trioleate, polysorbate 81, menthol, mineral oil, amyl cinnamal, cinnamal, citral, citronellol, geraniol, limonene, linalool, ethanol, algae extract, a C12-15 alkyl benzoate, *Centella asiatica* extract, cinnamidopropyltrimonium chloride, *citrus aurantium bergamia* fruit oil, *Elaeis guineensis* fruit extract, glycerin, soybean seed extract, rice extract, panthenol, *Plumeria acutifolia* flower extract, water, xylitol, a fragrance, and a flavoring agent.

The ointment may be obtained by heating the intermediate oil mixture with the sulfur, the petrolatum and the at least one agent configured for absorbing or blocking ultraviolet radiation at 60.0 to 70.0° C. for four hours.

The sulfur, petrolatum, and the at least one agent configured for absorbing or blocking ultraviolet radiation may be obtained from commercial sources, either as substantially pure components or as mixtures. For example, the sulfur and petrolatum can be obtained from Sulphur 8 Medicated Anti-dandruff Hair & Scalp Conditioner™ (J. Strickland & Co. Olive Branch, MS), which also contains lanolin, sorbitan trioleate, polysorbate 81, menthol, mineral oil, amyl cinnamal, cinnamal, citral, citronellol, geraniol, limonene, and linalool. Similarly, the avobenzone, homosalate, octisalate, and octocrylene may be obtained from COOLA Scalp and Hair Mist™ (Coola, LLC, Carlsbad, CA) which also contains ethanol, algae extract, a C12-15 alkyl benzoate, *Centella asiatica* extract, cinnamidopropyltrimonium chloride, *citrus aurantium bergamia* fruit oil, *Elaeis guineensis* fruit extract, glycerin, soybean seed extract, rice extract, panthenol, *Plumeria acutifolia* flower extract, water, xylitol, a fragrance, and a flavoring agent.

The present invention anticipates a production method for a hair or skin treatment composition. The production method comprises a first step of heating one or more of castor oil, animal fat, and vegetable oil with a mash comprising one or more of carrots, onions, coconut flesh, and watercress, for between one and eight hours. A second step of the production method entails filtering of a preliminary oil mixture to remove solids. A third step of the production method requires heating of the preliminary oil mixture with citrus juice and nutmeg for between one and eight hours. A fourth step of the production method entails straining of an intermediate oil mixture to remove solids. A fifth step of the production method requires heating of the intermediate oil mixture with sulfur, petrolatum, and at least one agent configured for absorbing or blocking ultraviolet radiation. A sixth step of the production method requires cooling of the product of the fifth step to provide the ointment.

In use, the hair or skin treatment composition enables a treatment method for hair or skin. The treatment method comprises a first step of providing an ointment per the specification. A second step of the treatment method entails applying a sufficient amount of the ointment to hair or skin to impart a physical or aesthetic property thereto. A third step of the treatment method includes allowing the ointment to remain in contact with the hair or skin until at least the next shampooing, showing, or bathing. A fourth step of the treatment method entails repeating application of the ointment to hair or skin after each shampooing, showing, or bathing, until a desired physical or aesthetic change to the skin or hair is obtained. The present invention provides protection from lice, treats and prevents dandruff in the hair, promotes hair growth, retention, and health, and provides protection from damage by ultraviolet radiation.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A hair or skin treatment composition comprising an ointment resulting from:
   heating one or more of castor oil, animal fat, and vegetable oil with a mash comprising one or more of carrots, onions, coconut flesh, and watercress, for between one and eight hours to generate, after straining to remove solids, a preliminary oil mixture;
   heating the preliminary oil mixture with one or more of citrus juice and nutmeg for between one and eight hours to generate, after straining to remove solids, an intermediate oil mixture; and
   heating the intermediate oil mixture with sulfur, petrolatum, and at least one agent configured for absorbing or blocking ultraviolet radiation to generate, upon cooling, an ointment configured for application to hair or skin of a user, wherein the at least one agent configured for absorbing or blocking ultraviolet radiation comprises avobenzone, homosalate, octisalate, and octocrylene; and
   wherein the preliminary oil mixture is derived from Haitian castor oil, chicken oil, cocoa oil, carrots, onions, coconut flesh, and watercress.

2. The hair or skin treatment composition of claim 1, wherein the preliminary oil mixture is derived from:
   16.00 to 21.00 weight percent Haitian castor oil;
   16.00 to 21.00 weight percent grams chicken fat;
   4.00 to 6.50 weight percent cocoa oil;
   7.50 to 10.00 weight percent carrots;
   15.00 to 20.00 weight percent onions;
   10.00 to 16.00 weight percent coconut flesh; and
   15.00 to 20.00 weight percent watercress.

3. The hair or skin treatment composition of claim 2, wherein the preliminary oil mixture is derived from:
   18.60 weight percent Haitian castor oil;
   18.60 weight percent chicken fat;
   5.30 weight percent cocoa oil;
   8.80 weight percent shredded carrots;
   17.70 weight percent shredded onions;
   13.30 weight percent grated coconut flesh; and
   17.70 weight percent watercress.

4. The hair or skin treatment composition of claim 1, wherein the intermediate oil mixture is derived from the preliminary oil mixture, citrus juice, and one of ground nutmeg and powdered nutmeg, wherein the citrus juice is lemon juice.

5. The hair or skin treatment composition of claim 2, wherein the intermediate oil mixture is derived from:
   85.00 to 96.00 weight percent the preliminary oil mixture, based on total weight of components thereof prior to heating;
   3.00 to 8.00 weight percent lemon juice; and
   0.50 to 2.00 weight percent of ground or powdered nutmeg.

6. The hair or skin treatment composition of claim 5, wherein the intermediate oil mixture is derived from:
   93.60 weight percent of the preliminary oil mixture, based on total weight of components thereof prior to heating;
   5.20 weight percent lemon juice; and
   1.20 weight percent of ground or powdered nutmeg.

7. The hair or skin treatment composition of claim 5, wherein the ointment is derived from:
   80.00 to 90.00 weight percent of the intermediate oil mixture, based on total weight of components thereof and the components of the preliminary oil mixture prior to heating;
   0.10 to 0.50 weight percent sulfur;
   10.0 to 20.0 weight percent petrolatum; and
   0.03 to 0.09 weight percent avobenzone;
   0.10 to 0.20 weight percent homosalate;
   0.10 to 0.20 weight percent octisalate; and
   0.10 to 0.20 weight percent octocrylene.

8. The hair or skin treatment composition of claim 7, wherein the ointment is derived from:
   84.70 weight percent of the intermediate oil mixture, based on total weight of components thereof and the components of the preliminary oil mixture prior to heating;
   0.30 weight percent sulfur;
   14.50 weight percent petrolatum;
   0.06 weight percent avobenzone;
   0.14 weight percent homosalate;
   0.12 weight percent octisalate; and
   0.16 weight percent octocrylene.

9. A hair or skin treatment composition comprising an ointment resulting from:
   heating one or more of castor oil, animal fat, and vegetable oil with a mash comprising one or more of carrots, onions, coconut flesh, and watercress, for between one and eight hours to generate, after straining to remove solids, a preliminary oil mixture;
   heating the preliminary oil mixture with one or more of citrus juice and nutmeg for between one and eight hours to generate, after straining to remove solids, an intermediate oil mixture;
   heating the intermediate oil mixture with sulfur, petrolatum, and at least one agent configured for absorbing or blocking ultraviolet radiation to generate, upon cooling, an ointment configured for application to hair or skin of a user, wherein the at least one agent configured for absorbing or blocking ultraviolet radiation comprises avobenzone, homosalate, octisalate, and octocrylene; and
   at least one of lanolin, sorbitan trioleate, polysorbate 81, menthol, mineral oil, amyl cinnamal, cinnamal, citral, citronellol, geraniol, limonene, linalool, ethanol, algae extract, a C12-15 alkyl benzoate, *centella asiatica* extract, cinnamidopropyltrimonium chloride, *citrus*

*aurantium bergamia* fruit oil, *Elaeis guineensis* fruit extract, glycerin, soybean seed extract, rice extract, panthenol, *plumeria acutifolia* flower extract, water, xylitol, a fragrance, and a flavoring agent.

10. A hair or skin treatment composition comprising an ointment resulting from;
   heating one or more of castor oil, animal fat, and vegetable oil with a mash comprising one or more of carrots, onions, coconut flesh, and watercress, for between one and eight hours to generate, after straining to remove solids, a preliminary oil mixture;
   heating the preliminary oil mixture with one or more of citrus juice and nutmeg for between one and eight hours to generate, after straining to remove solids, an intermediate oil mixture;
   heating the intermediate oil mixture with sulfur, petrolatum, and at least one agent configured for absorbing or blocking ultraviolet radiation to generate, upon cooling, an ointment configured for application to hair or skin of a user, wherein the at least one agent configured for absorbing or blocking ultraviolet radiation comprises avobenzone, homosalate, octisalate, and octocrylene;
   wherein the one or more of castor oil, the animal fat, and the vegetable oil and the mash comprising one or more of the carrots, the onions, the coconut flesh, and the watercress are heated at 80.0 to 100.0° ° C. for four hours;
   wherein the preliminary oil mixture and the one or more of the citrus juice and the nutmeg are heated at 100.0 to 150.0° ° C. for four hours; and
   wherein the intermediate oil mixture, the sulfur, the petrolatum, and the at least one agent configured for absorbing or blocking ultraviolet radiation are heated at 60.0 to 70.0° ° C. for four hours.

\* \* \* \* \*